United States Patent [19]

Paulus

[11] Patent Number: 5,523,210
[45] Date of Patent: * Jun. 4, 1996

[54] BISPECIFIC ANTIBODY DETERMINANTS

[75] Inventor: Henry P. Paulus, Boston, Mass.

[73] Assignee: Boston Biomedical Research Institute, Inc., Boston, Mass.

[*] Notice: The portion of the term of this patent subsequent to Mar. 8, 2011, has been disclaimed.

[21] Appl. No.: 900,514

[22] Filed: Jun. 17, 1992

Related U.S. Application Data

[63] Continuation of Ser. No. 603,125, Apr. 23, 1984, abandoned, which is a continuation-in-part of Ser. No. 332,881, Dec. 21, 1981, Pat. No. 4,444,878.

[51] Int. Cl.$^6$ .................... G01N 33/563; C07K 16/46
[52] U.S. Cl. .................... 435/7.91; 436/537; 436/546; 436/548; 436/819; 530/387.3
[58] Field of Search ............... 435/18, 25, 28, 435/174, 179, 175, 178, 288, 291, 177, 188, 805, 810, 4, 817, 8, 172.2, 240, 7.93, 7.91; 436/512, 513, 518, 528, 548, 808, 806, 819, 530, 537, 546; 530/387.3

[56] References Cited

U.S. PATENT DOCUMENTS

| | | | |
|---|---|---|---|
| 4,233,402 | 11/1980 | Maggio et al. | 435/7 |
| 4,331,647 | 5/1982 | Goldenberg | 435/172.2 |
| 4,340,535 | 7/1982 | Voisin et al. | 435/172.2 |
| 4,350,626 | 9/1982 | Masuho et al. | 935/107 |
| 4,433,059 | 2/1984 | Chang et al. | 436/512 |
| 4,446,233 | 5/1984 | Auditore-Hargreaves | 435/7 |
| 4,470,925 | 9/1984 | Auditore-Hargreaves | 435/188 |
| 4,474,893 | 10/1984 | Reading | 435/7 |
| 4,520,110 | 5/1985 | Stryer et al. | 436/501 |
| 4,542,104 | 9/1985 | Stryer et al. | 436/537 |

FOREIGN PATENT DOCUMENTS

| | | | |
|---|---|---|---|
| 83/03679 | 10/1983 | WIPO | 435/7 |

OTHER PUBLICATIONS

Glennie, "Bispecific Antibody in the Treatment of Neoplastic Disease", ISBT Communications, vol. 3, No. 2, (1988).
Glennie et al., "Preparation and Performance of Bispecific F(ab'γ Fragments", J. of Imunology, vol. 139, 2367, (1987).
Nielsen et al., "Monoclonal Antibodies in Veterinary Medicine", Biology and Genetic Engineering Reviews, vol. 4, (1986).
Kelley et al., "Monoclonal Antibodies: Pragmatic Application of Immunology and Cell Biology", J. Anim. Sci, 63:288, (1986).
Hammerling et al, J. Exp. Med., 128:1461–1469 (1968).
Lamoyi et al, J. Immunol. Meth., 56: 235–243 (1983).
Nisonoff et al. (1964), Science 134, 376–379.
Nisonoff et al. (1960), Arch. Biochem. Biophys. 89, 230–244.
Nisonoff and Rivers (1960), Arch Bichem. Biophys. 93, 460–462.
Nisonoff (Nov. 2, 1981), Current Contents 44, 25.
Raso and Griffin (1978), Fed. Proc. 37, 1350.
Milstein (1981), Proc. R. Soc. Lond. B211, 393–409.
Schwaber et al. (1974), P.N.A.S. USA 71, 2203–2207.
Cotton et al. (1973), Nature 244, 42–43.
Raso et al. (1981), Cancer Research 41, 2073–2078.
Rechnitz (1981), Science 214, 287–291.
Galfre et al. (1981), Methods in Enzymology 73, 3–46.
Ey et al. (1978), Immunochemistry 15, 429–436.
Hackett et al. (1981), Immunology 4, 207–215.
Raso and Griffin (1980), J. Immunol. 125, 2610–2616.
Karube et al. (1972), 47, 51–54.
Satoh et al. (1976), Biotechnol. and Bioengineering 18, 269–272.
Cuatrecasas et al. (1968), Proc. Nat'l. Acad. Sci. USA 61, 636–643.
Bayer et al. (1974), Methods in Enzymology 34B, 265–267.
M. W. Turner, Chapt. 1 "Structure and Function of Immunoglobulins" in *Immunochemistry: An Advanced Textbook*, L. E. Glynn and M. W. Steward, Eds., John Wiley & Sons, (Chichester, New York, Brisbane, Toronto: 1977).

*Primary Examiner*—Mary E. Ceperley
*Attorney, Agent, or Firm*—Fish & Richardson

[57] ABSTRACT

A homogenous sample of identical bispecific antibody determinants, each determinant being composed of two L-H half-molecules linked by disulfide bonds, each L-H half-molecule being specific for a different antigenic determinant and including at least the F(ab') portion of a monoclonal IgG antibody. The bispecific antibody determinants are useful, e.g., in the formation of multilamellar assemblies and in enzymatic assays.

42 Claims, 9 Drawing Sheets

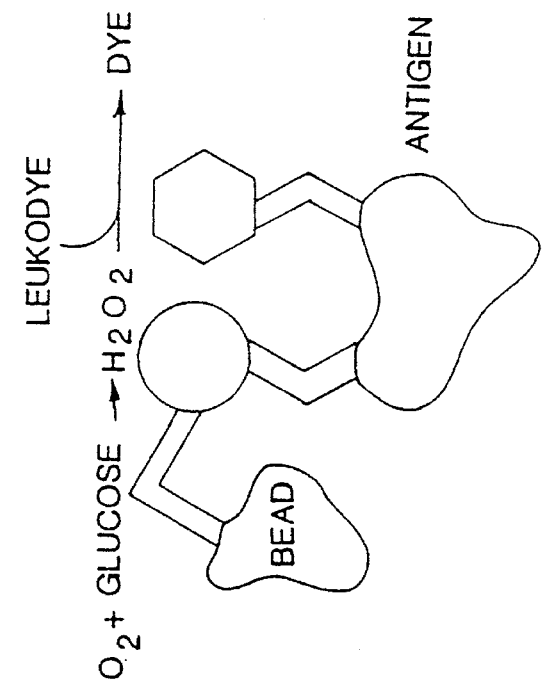
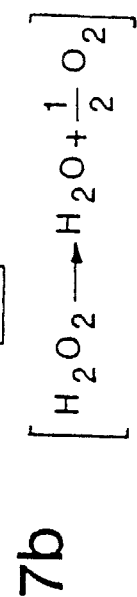
FIG. 7b
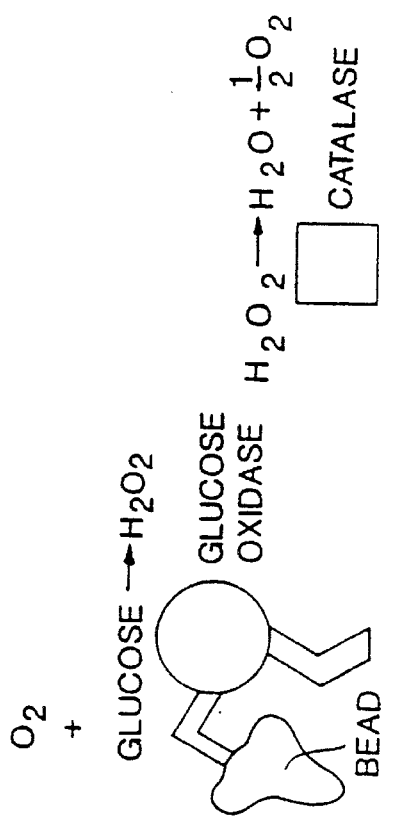
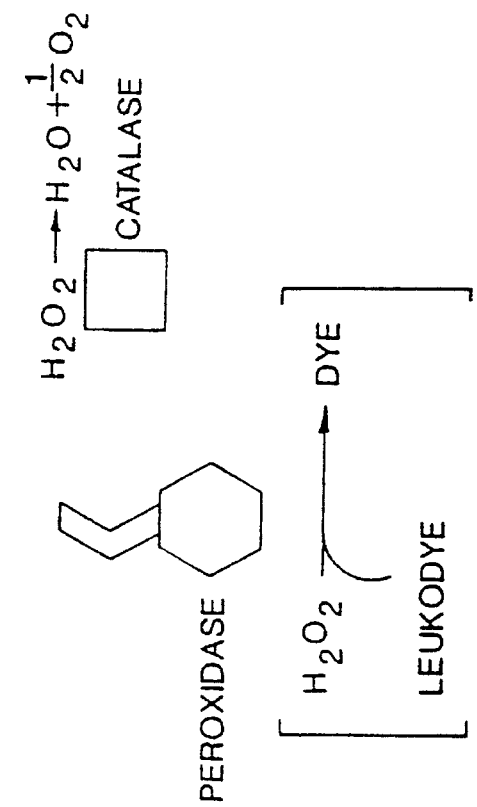
FIG. 7a

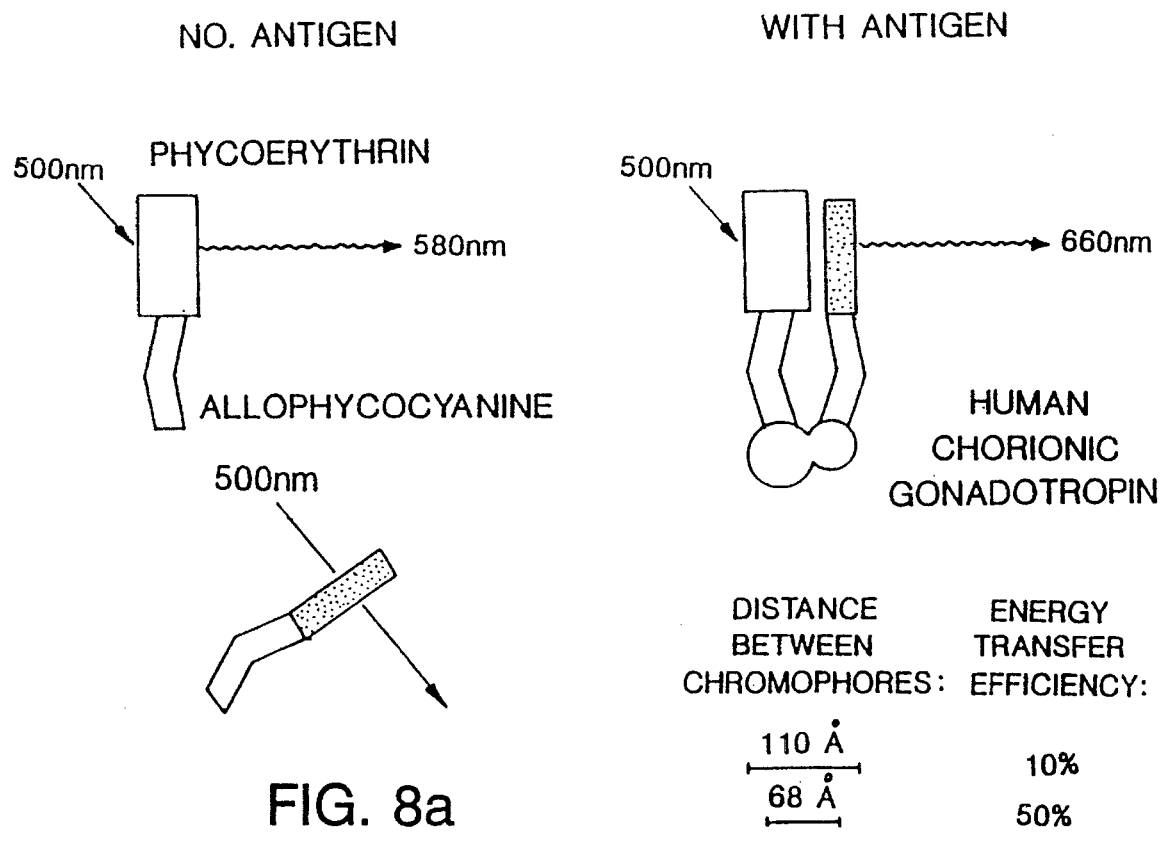

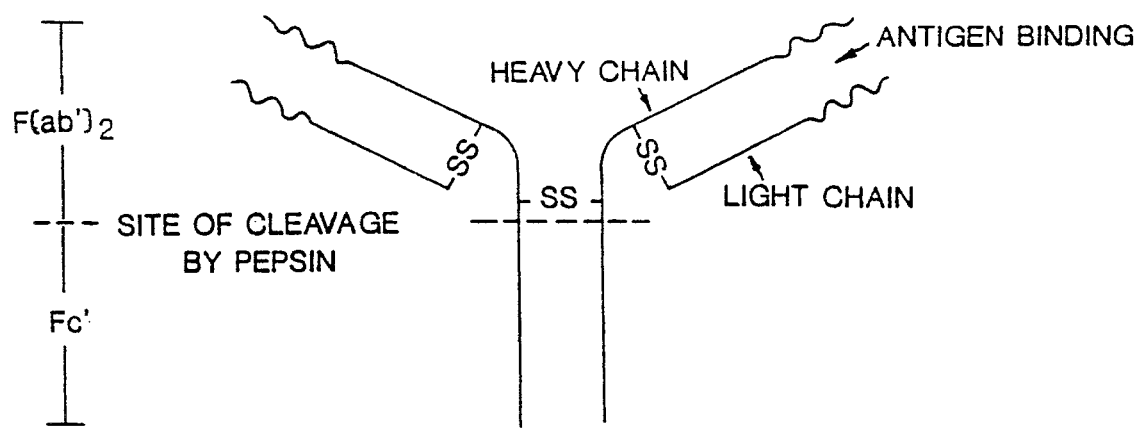
RABBIT IgG$_1$  FIG. 9a
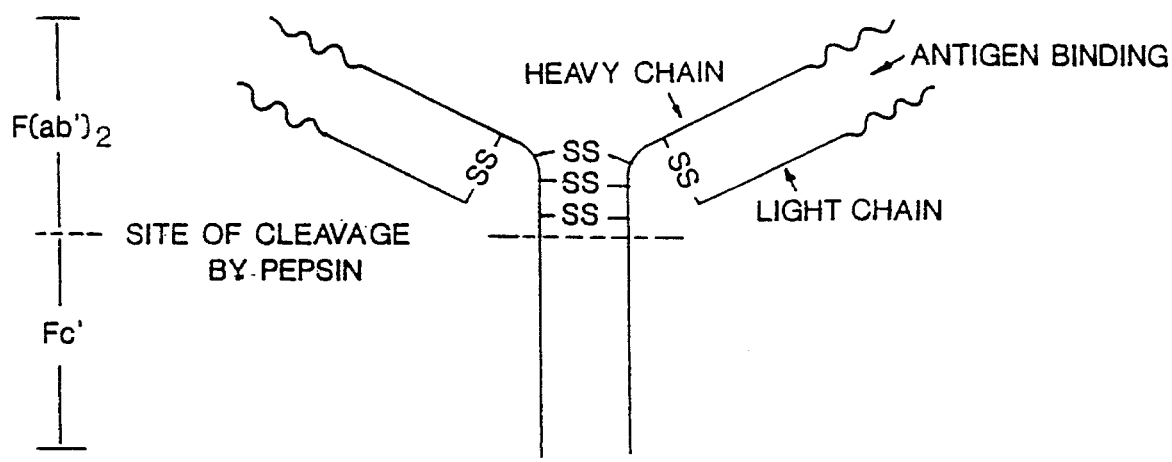
MOUSE IgG$_1$  FIG. 9b

1. PREPARATION OF Fab' THIONITROBENZOATE (TNB) DERIVATIVES

2. PREPARATION OF Fab' THIOL ARSENITE DERIVATIVES

3. PREPARATION OF PURE BISPECIFIC ANTIBODY

BISPECIFIC ANTIBODY DETERMINANTS

This is a continuation of application Ser. No. 06/603,125, filed Apr. 23, 1984, now abandoned which is a continuation-in-part of Paulus U.S. patent application Ser. No. 332,881, filed Dec. 21, 1981, now U.S. Pat. No. 4,444,878.

The IgG antibodies are known to consist of two half-molecules, each consisting of a light (L) chain and a heavy (H) chain. The H chains of the two halves are linked by disulfide bonds, which can be broken by selective reduction. If this step is performed for two different IgG samples, the half-molecules can be combined to form hybrid antibodies. This has been accomplished using intact rabbit globulins; Nisonoff et al. (1964) Science 134, 376–379. The IgA antibodies can also be split into identical half-molecules.

Hybrids have also been formed using the F(ab')$_2$ fragments of IgG antibodies, rather than intact antibodies; i.e., the F(c') portions of the molecules, which do not provide immunospecificity, are, prior to hybridization, removed by digestion with an appropriate protease such as pepsin. This procedure has been described in Nisonoff et al. (1960) Arch. Biochem. Biophys. 89, 230–244 and in Nisonoff and Rivers (1960) Arch. Biochem. Biophys. 93, 460–462. In a later discussion of the first paper Nisonoff wrote, in Current Contents (Nov. 2, 1981) 44, 25:

> So far this procedure has had limited application, principally in the staining of cell surfaces with ferritin by using a hybrid of anti-ferritin antibody and antibody to a cell surface antigen. The use of hybrid antibody has also been considered as a means of bringing a pharmacological agent specifically into contact with a desired tissue surface.

The use of such hybrids for the delivery of cytotoxic drugs has also been suggested in Raso and Griffin (1978) Fed. Proc. 37, 1350.

Milstein (1981) Proc. R. Soc. Lond. B211, 393–412 suggests the possibility of using "monoclonal antibodies as carriers of toxic substances for specific treatment of tumors," and states that "(i)t is possible that Fab fragments will be better targeting agents than intact antibody."

Hybrid antibodies have also been formed by fusing two cells, each capable of producing different antibodies, to make a hybrid cell capable of producing hybrid antibodies. Such a method is described in Schwaber et al. (1974) P.N.A.S. USA 71, 2203–2207. Mouse myeloma cells were fused to human lymphocytes, and the resultant fused cells produced "hybrid antibody molecules containing components of mouse immunoglobulins assembled with human heavy and light chains." The human antibody component was not monoclonal, and was undefined.

Schwaber et al. also describes an in vitro experiment in which the mouse and human antibodies were reduced strongly enough to break bonds between L and H chains, and then "allowed to recombine randomly."

In Cotton et al. (1973) Nature 244, 42–43 there is described an experiment in which mouse myeloma cells were fused to rat tumor cells to produce fusions which produced "an extra component" which was "likely . . . a hybrid mouse-rat light chain dimer" as well as "non-symmetrical molecules made up of one light chain of each parental type."

Another paper, Raso et al. (1981) Cancer Research 41, 2073–2078, describes the formation of an impure sample of rabbit antibody F(ab')$_2$ fragments against human IgG F(ab')$_2$ fragments; the rabbit antibody fragments were split by reduction and reassembled with antiricin A chain F(ab')$_2$ fragments. The dual specificity dimers were used in targeted drug delivery experiments. The article states:

> The two types of purified antibodies used for this work were isolated from conventional heteroantisera. Thus, a complicated array of affinity and specificity combinations must arise upon annealing these two populations. The advent of homogenous hybridoma-derived antibodies will afford absolute control over the binding affinities of the constituent halves of a hybrid antibody, and this uniformity should greatly boost their ultimate effectiveness as delivery vehicles.

The present invention provides a homogenous sample of identical bispecific antibody determinants, each bispecific determinant being composed of two L-H half-molecules linked by disulfide bonds, each L-H half-molecule being different from the other and being specific for a different antigenic determinant.

The bispecific monoclonal antibody determinants of the invention are made by providing two different monoclonal antibody determinants, each composed of two identical L-H half-molecules linked by one or more disulfide bonds; subjecting the two different antibody determinants to conditions sufficient to break the disulfide bonds linking the L-H half-molecules, whereby each determinant is split into a pair of identical half-molecules; and combining the half-molecules under conditions which permit them to chemically combine to form the bispecific antibody determinants by the formation of one or more disulfide bonds.

Preferably the process further includes, prior to the combining step, derivatizing one pair of identical half-molecules with a thiol activating agent which facilitates the formation of the disulfide bonds between the thiol activated half-molecules and the different half-molecules.

In other preferred embodiments, the monoclonal antibodies are IgG (most preferably IgG$_1$, or, less preferably, IgG2A, IgG2B, or IgG3) or IgA; each half-molecule, if derived from an IgG antibody, includes at least the F(ab') portion; the thiol activating agent prevents the recombination of the thiol activated half-molecules; one or both of the monoclonal antibody determinants is composed of half-molecules linked by more than one disulfide bond, and the step of splitting such determinants into half-molecules is carried out under conditions which prevent the formation of disulfide bonds within the H chains of the half-molecules; and the thiol activating agent is 5,5'-dithiobis (2-nitrobenzoic acid), 2,2'-dipyridine disulfide, 4,4-dipyridine disulfide, or a mixture of sulfite and thiosulfite. (The use of thiol activating agents to link F(ab') fragments to other proteins has been described, e.g., in Raso et al. (1980) J. Immunol. 125, 2610; Raso et al. (1982) Cancer Res. 42, 457; and Masuho et al. (1979) B.B.R.C. 90, 320, hereby incorporated by reference.) Preferably the formation of disulfide bonds within the H chains of half-molecules originally linked by disulfide bonds is prevented by carrying out the splitting reaction in the presence of a dithiol complexing agent such as an arsenite, e.g., an inorganic arsenite such as sodium arsenite, or an aryl arsenite, e.g., phenylarsine oxide, or a cadmium salt, or by carrying out the splitting reaction under conditions under which the conformation of the H chains is modified to prevent disulfide bond formation, e.g., at a pH between 3.8 and 4.5 (most preferably 4.2), or by removing all but one reduced cystsine residue using a proteolytic enzyme such as carboxypeptidase Y.

Where the recombination of like half-molecules with each other is prevented purification of bispecific determinants from the mixture can be carried out simply on the basis of molecular size, e.g. by gel filtration; this is possible because the only molecules in the solution, half-molecules and bispecific hybrids, are different in size by a factor of two. An alternative, less preferred separation method is affinity chromatography, involving contacting the mixture with an affinity matrix containing an antigen capable of specifically binding to either of the two halves of the bispecific antibody determinant, then eluting matrix-bound material, and contacting that material with an affinity matrix containing an antigen capable of specifically binding the other half-molecule. The material bound to this second matrix has the required dual specificity.

Another alternative, less preferred separation method can be used in a case where one of the halves of the bispecific antibody determinant has a specificity for an antigenic determinant which is a macromolecule (a molecule having a molecular weight greater than about 1000 daltons). This method involves adding the macromolecular antigenic determinant to the sample containing the bispecific antibody determinant to be purified to form immune complexes which can be separated into subfractions having different molecular weights by, e.g., gel filtration or electrophoresis. The subfraction having a molecular weight equivalent to the molecular weight of the complex of the desired bispecific antibody determinant with the macromolecular antigen is separated from the other subfractions, and, if desired, the macromolecular antigen is then removed using conventional methods. Other separation methods are, e.g., ion exchange and isoelectric focusing.

IN THE DRAWINGS

FIG. 7 is a diagrammatic representation of a channeling immunoassay employing bispecific monoclonal antibody determinants.

FIG. 8 is a diagrammatic representation of a fluorescent energy transfer immunoassay employing bispecific monoclonal antibody determinants.

FIG. 9 is a diagrammatic representation showing the structure of rabbit $IgG_1$ compared to mouse $IgG_1$.

Figure 1:
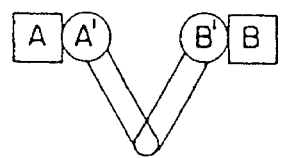
FIG. 1 is a diagrammatic representation of two different antigenic determinants linked by a bispecific antibody determinant.

The bispecific monoclonal antibody determinants of the invention are useful for a wide range of applications. Referring to FIG. 1, these applications all flow from the ability of these determinants to serve as highly specific linkers through specific sites A' and B', of any two antigenic determinants A and B capable of stimulating antibody production in animals; e.g., effective proteins. polypeptides, carbohydrates, nucleic acids, or haptens, either free or immobilized on surfaces or particles.

One application of the bispecific antibody determinants of the invention is their use as agents for bonding a desired antigenic entity to a desired surface which contains or has immobilized on it a different antigenic determinant. For example, enzymes so immobilized on particles or membranes can be used as solid-state catalysts. Advantages of this type of immobilization over others are that antibodies can be selected which have no adverse effect on enzyme activity, and that pure enzymes can be immobilized from impure mixtures. Bispecific antibody determinants can also be used as highly specific bispecific reagents for immunoassay procedures which are used, e.g., in the diagnosis of medical disorders, or as molecular probes to study the relationships between antigenic determinants in biological systems.

An additional application of the bispecific antibody determinants is their use in electrodes. Currently-used enzyme electrodes frequently employ tissue slices as the enzyme source. For example, electrodes for measuring glutamine have been made using a conventional $NH_3$ electrode in combination with kidney slices as the source of glutaminase, the enzyme which breaks down glutamine to produce measurable $NH_3$ ions; Rechnitz (1981) Science 214, 287–291.

The present invention provides electrode apparatus for the measurement in a sample of an unknown amount of a substance which is acted on by one or more enzymes to evolve a measurable ion or compound, the ion or compound evolved being a measure of the unknown substance. The electrode apparatus includes means for measuring the measurable ion or compound, and, associated with that means, a membrane having associated therewith a plurality of molecules of each enzyme which acts on the substance to be measured and, bonded to the molecules of each enzyme, a plurality of identical, bispecific antibody determinants. Each determinant is composed of two different L-H half-molecules linked by disulfide bonds, and each half-molecule includes at least the F(ab') portion of a monoclonal IgG antibody. One said L-H half-molecule is specific for an antigenic site on the enzyme molecule to which it is bonded and the other half-molecule is specific for an antigenic determinant on the membrane to which the bispecific antibody determinant is bonded to become immobilizably associated with the membrane.

The electrode can be used to measure any substance which can be metabolized by an enzyme or combination of enzymes in a way which produces or consumes a measurable ion or compound such as $NH_3$, $CO_2$, $O_2$, or $H^+$, provided that each enzyme can bind specifically to a site on an immobilized bispecific antibody determinant.

Figure 2:
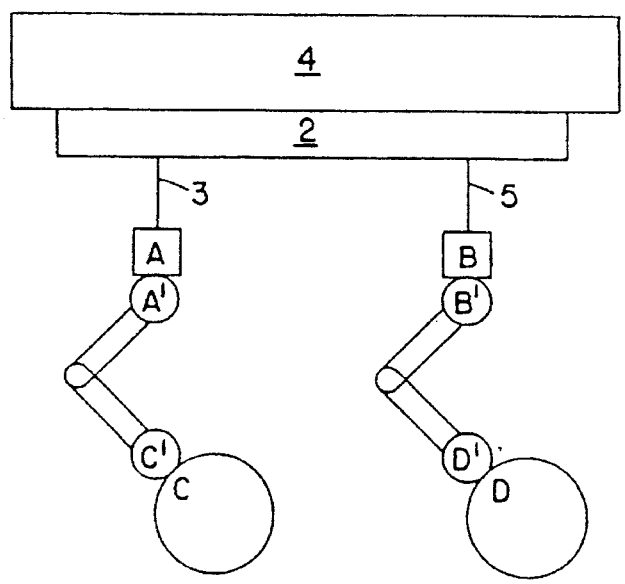
FIGS. 2 and 3 are diagrammatic representations of electrodes employing bispecific antibody determinants.
Figure 3:
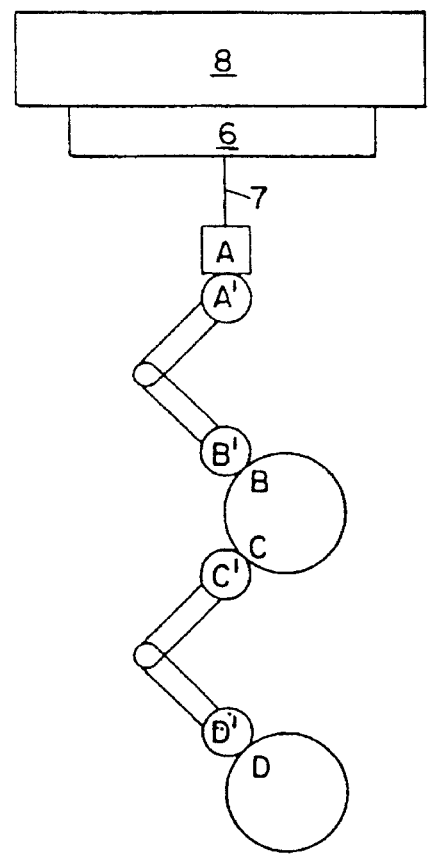

The reaction can be one which requires more than one enzyme. It is required in such a case that all of the required enzymes be immobilized on bispecific antibody determinants which are immobilized in the electrode. FIGS. 2 and 3 illustrate two modes of enzyme immobilization in a two-enzyme system in which the two enzymes catalyze consecutive reactions in the conversion of a substance to an ion or compound which can be measured by the appropriate ion or compound-specific membrane electrode. The invention can be used in electrodes of any configuration, e.g. in solid state sensors such as field effect transistors, e.g., as described in Wohltjen (1984) Analyt. Chem. 56, 87A.

Referring to FIG. 2, membrane 2 of electrode 4 bears, on spacer arms 3 and 5, different haptens A and B, in the desired ratio, to which are immobilized different bispecific antibody determinants having, respectively, hapten-specific sites A' and B'. The second site on each bispecific antibody determinant is specific, respectively, for binding sites on enzymes C and D, which catalyze consecutive steps in the breakdown of the substance to be measured into a measurable compound or ion.

Referring to FIG. 3, membrane 6 of electrode 8 bears, on spacer 7, hapten A, to which is immobilized a bispecific antibody determinant having hapten A-specific site A' and a second site, B', which is specific for binding site B on one of the two enzymes necessary for the breakdown of the substances to be measured into a measurable compound or ion. The second bispecific antibody determinant has a site, C', specific for antigenic binding site C on the first enzyme, and a second site, D', specific for a different antigenic binding site D on the second enzyme required for the production of the measurable compound or ion. The advantage of the arrangement shown in FIG. 3 is that it assures that the two enzymes are closely linked so that the two reactions are efficiently coupled.

Enzyme electrodes made using bispecific antibody determinants possess several advantages over conventional enzyme electrodes. One advantage is their precise self-assembling property: the desired electrode assembly is generated simply by attaching the appropriate hapten or haptens to the membrane (either the electrode membrane or a separate membrane associated with the electrode) and then immersing the hapten-derived membrane into a solution containing the appropriate bispecific antibodies and enzymes. This ease of assembly also means that the electrode can be easily recharged after deterioration has occurred through prolonged use.

Another advantage of the electrodes is also a function of the specificity of the bispecific antibody determinants. Any given enzyme will possess a number of antigenic sites capable of binding to a specific site of an antibody. However, coupling at many of these sites can cause inactivation of the enzyme. In the case of bispecific monoclonal antibody determinants, this problem is avoided because the determinants are selected so that they couple with the enzyme only at a site which does not cause deactivation of the enzyme.

A further advantage is that assembly or recharging of the electrode can be done with impure enzyme mixtures because the unique specificity of the bispecific antibody determinants assures the selection of the proper enzymes from the impure mixture.

In some instances the membrane containing the immobilized enzymes can be covered with a second semipermeable membrane to slow the deterioration of the electrode assembly, or the assembly can be stabilized by treatment with glutaraldehyde or with another mild bifunctional cross linker, e.g., dimethyl suberimidate.

Yet another application for the bispecific antibody determinants is their use in the formation of self-assembling networks for use, e.g., as molecular microcircuits. Such a network is illustrated diagrammatically in FIG. 4, wherein A, B, C, D, E, and F represent antigenic determinants and A', B', C', D', E', F', represent, respectively, corresponding antibody determinants. It can be seen that the number of linked specific determinants is virtually limitless and, further, that the network can be highly complex and in two or three dimensions. Most importantly, the network, no matter how complex, is entirely self-assembling in a uniquely defined way.

One example of such a self-assembling network is a multilamellar assembly for use, e.g., in chemical assays or in the production of specific chemicals in industrial processes. Currently used assemblies for assays of substances in, e.g., serum, employ a series of layers of enzymes trapped between membranes of low porosity. The sample containing the substance to be measured is placed on the outer surface of the assembly and allowed to seep down through the layers, interacting successively with the trapped enzymes until, in the bottom layer, measurable result is produced, e.g. luminescence, fluorescence, or a color change; this result is a measure of the substance being measured in the sample.

Figure 4:
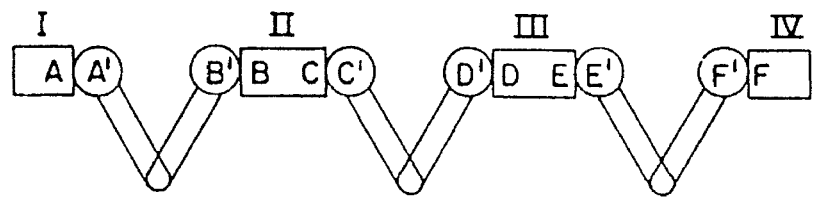
FIG. 4 is a diagrammatic representation of a self-assembling network employing bispecific antibody determinants.

The multilamellar assembly of the invention employs bispecific antibody determinants to link two or more enzymes which can be sequentially acting, as illustrated in FIG. 4 (I–IV representing different enzymes). The low-porosity membranes of current assemblies are thus in many instances unnecessary, the spatial relationships among the enzymes already being fixed by their attachment to bispecific antibody determinants. Furthermore, the use of bispecific antibody determinants to link enzymes enhances the efficiency of the reaction by reducing the diffusion time of intermediates.

In the multilamellar assemblies of the invention, the antigenic determinants linked by the bispecific antibody determinants are, in some cases, not enzymes but other catalysts e.g., microbial cells. This will be the case in certain industrial processes, for example, in which the goal of the process is not the measurement of a compound but the production of a desired chemical via a series of chemical reactions.

We turn now to a more detailed discussion of the formation of the bispecific antibody determinants of the invention, and to the particular method used where the antibodies are of mouse origin.

Figure 10A:
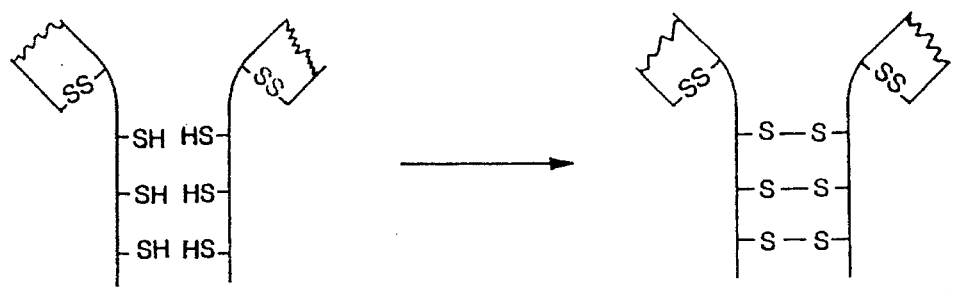
FIG. 10 is a diagrammatic representation of competing intrachain disulfide reactions in mouse half-molecules.
Figure 10B:
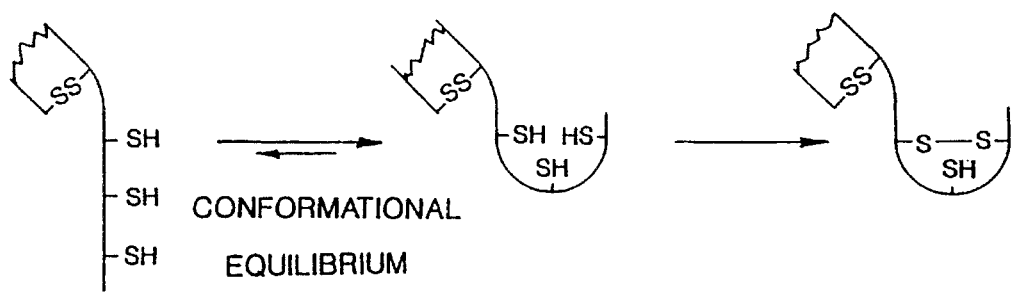

FIG. 9 illustrates the difference in structure between rabbit $IgG_1$ antibodies and mouse $IgG_1$ antibodies (which comprise most monoclonal antibodies.) These structures differ in the number of disulfide bonds linking the heavy chains. The two halves of rabbit $IgG_1$ are held together by a single bond, and the reduction of $F(ab')_2$ to $F(ab')$ monomer as well as the reassociation of monomer to the dimer thus involves the breakage and reformation of only one bond, a relatively simple process. In contrast, the heavy chains of mouse $IgG_1$ are linked by 3 disulfide bonds, and their breakage and reformation can lead to competing intrachain side reactions of the type illustrated in FIG. 10, which can significantly diminish the yield of desired product. The intrachain reaction renders the half-molecule unavailable for combination with a different half-molecule. The method of the invention allows the production of pure bispecific monoclonal antibody determinants in high yield, from mouse monoclonal antibodies as well as from antibodies derived from other mammalian species.

The method involves the following sequence of steps. Using conventional methods, two different monoclonal $IgG_1$ antibody samples are produced, each antibody having one of two desired specificities. Each sample is then exposed to an appropriate protease such as pepsin to cleave off the F(c') portion of the antibody molecule to produce an $F(ab')_2$ fragment. Each sample is then subjected to conditions sufficient to break the disulfide bonds linking the F(ab') half-molecules, but not any of the other disulfide bonds in the molecule. At the same time, these conditions are such as to prevent the formation of disulfides within a single heavy chain, for example by the addition of a dithiol complexing agent (e.g. sodium arsenite (as shown in FIG. 11), an aromatic arsenite such as phenylarsine oxide, or $CdCl_2$), or by modifying the conformation of the heavy chain (e.g. by lowering the pH to 4.2), or by removing all but one of the reduced cysteine residues with a proteolytic enzyme (e.g. carboxypeptidase Y).

Figure 11A:
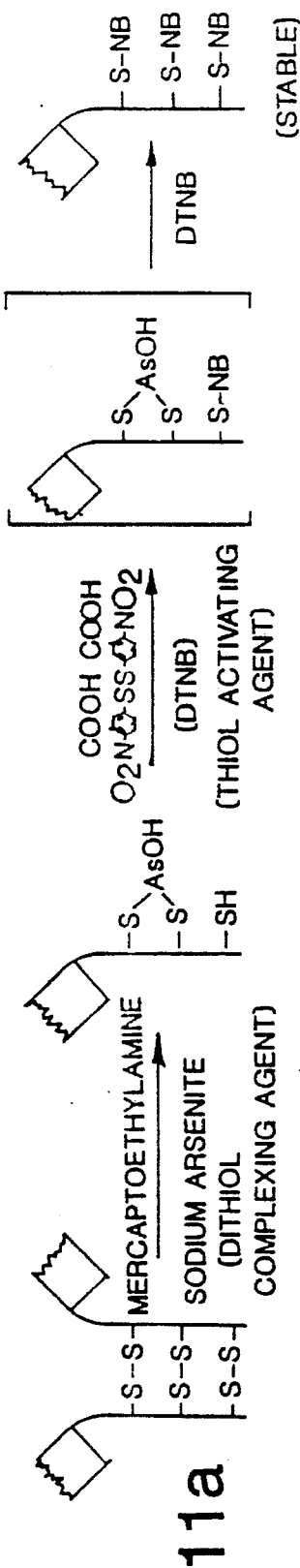
FIG. 11 is a diagrammatic representation of a preferred method of preparing bispecific monoclonal antibody determinants.
Figure 11B:
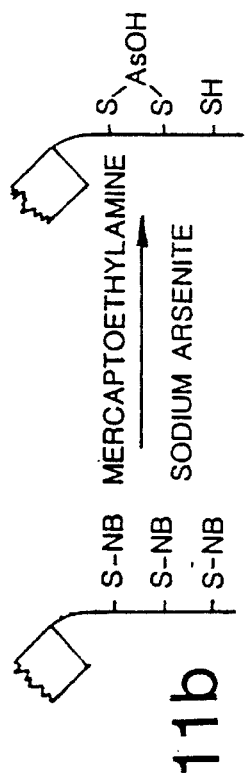
Figure 11C:
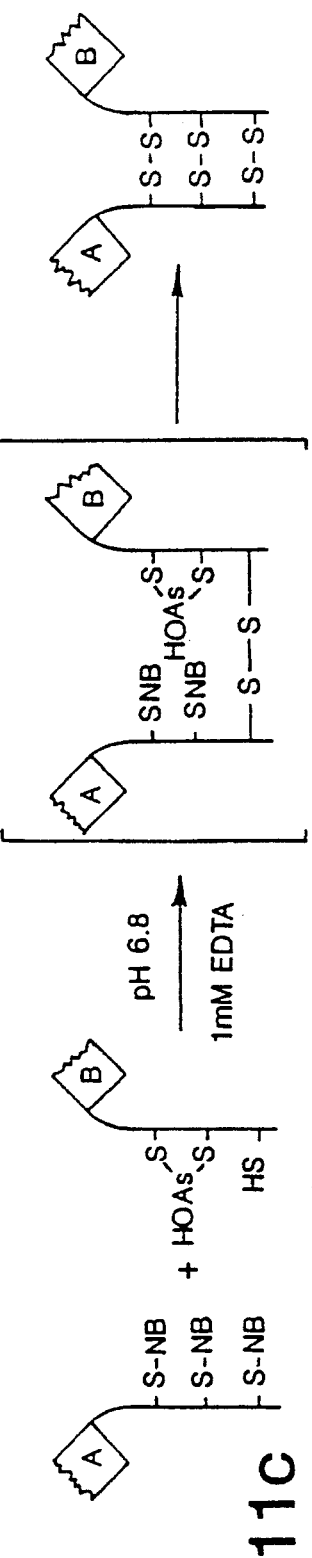

One of the samples is then exposed to a thiol-activating agent to complex all free thiols, forming a derivative that can react rapidly with other free thiols to form disulfides, as shown at the end of sequence 1 in FIG. 11. Among the agents suitable for this purpose are aromatic disulfides such as DTNB (Ellman (1959) Arch. Biochem. Biophys. 82, 70) (FIG. 11), 2,2'-dipyridine disulfide, 4,4'-dipyridine disulfide (Grasetti et al. (1967) Arch. Biochem. Biophys. 119, 41) and sulfite/thiosulfate (Masuho et al. (1979) B.B.R.C. 98, 320). This activated sample is then combined (sequence 3 of FIG. 11) with the other dithiol complexed sample, which has available thiols, under conditions where at least some half-molecules combine chemically to form bispecific antibody determinants but no monospecific $F(ab')_2$.

Alternatively, both samples can be exposed to the thiol-activating agent to form the activated thiol derivatives. (This is frequently convenient because of the relatively good stability of the activated derivatives.) One of the samples is then treated with an excess of a low molecular weight thiol to regenerate the free thiols on the F(ab') monomer, followed by separation from excess low molecular thiols under conditions where intramolecular disulfide bond formation is avoided. If necessary, this can be accomplished by the addition of a dithiol complexing agent (sequence 2 of FIG. 11) or by modifying the conformation of the heavy chain. This sample is then combined (sequence 3 of FIG. 11) with the other F(ab') sample in the thiol-activated form under conditions where at least some half-molecules combine chemically to form bispecific $F(ab')_2$.

Since the $F(ab')_2$ fraction produced under those conditions consists only of the desired bispecific antibody determinants, provided appropriately purified monoclonal antibodies have been used as starting materials, homogenous bispecific antibody determinants can be obtained simply by removing the monomeric F(ab') fraction from the desired $F(ab')_2$ on the basis of molecular size, by a convenient procedure such as gel filtration.

The following procedure is used to prepare a homogenous sample of identical bispecific antibody determinants in which each bispecific determinant has a site specific for a unique antigenic site on the protein avidin, and a site specific for a unique antigenic site on the enzyme β-galactosidase. This procedure follows the steps generally illustrated in FIG. 11.

The first step is the preparation of monoclonal antibodies against the two proteins avidin and β-galactosidase. This is done by first immunizing one group of BALB/C mice against each enzyme using standard immunization procedures.

Following immunization, spleen cells of immunized animals are prepared and fused with a derivative of MOPC-21 myeloma cells (e.g., NS1 or SP2/O-Ag14) using the procedure described in Galfre et al. (1981) Methods in Enzymology 73, 3–46. The hybrid cells are selected in hypoxanthine-aminopterin-thymidine medium, cloned, and screened for production of antibodies against the desired enzymes by the method described in Galfre et al. Id. The clones found to produce antibodies against the desired enzyme are then screened to select a clone which produces an antibody of the $IgG_1$ class which has a high affinity for the enzyme and which does not cause inactivation of the enzyme. The clones of interest are stored until use under liquid nitrogen. Antibody is prepared by the standard technique of propagating the cloned cells as ascitic tumors in the peritoneal cavities of pristane-primed mice.

The desired $IgG_1$ antibodies against avidin and β-galactosidase are then purified from ascites fluid essentially as described by Parham et al. (1982) Journal of Immunological Methods 53, 133–173, by a procedure involving ammonium sulfate precipitation, gel filtration, and chromatography on DEAE cellulose with a linear salt gradient. The monoclonal antibodies are cleaved to $F(ab')_2$ fragments with pepsin as described by Lamoyi and Nisonoff (1983) Journal of Immunological Methods 56, 235–243 by incubating for 18 hours at 25° C. with pepsin (2% by weight) in 0.1M sodium acetate, pH 4.2. The $F(ab')_2$ fragments are then purified by high performance liquid chromatography on a TSK 3000 SW column in 0.1M sodium phosphate, pH 6.8, as described in Parham et al. Id.

The $F(ab')_2$ fractions are then completely converted to Fab' monomer by reduction with 1 mM 2-mercaptoethylamine in 1 mM EDTA, 10 mM sodium arsenite, and 0.1M sodium phosphate, pH 6.8, for 18 hours at 25° C. The protein is then exchanged into a fresh solution of 1 mM 2-mercaptoethylamine, 1 mM EDTA, 10 mM sodium arsenite, and 0.1M sodium phosphate, pH 6.8, by centrifugal gel filtration on Sephadex G-25, and supplemented with solid DTNB to final concentration of 5 mM. After 2–3 hours at 25° C., excess DTNB and low molecular weight products are removed by centrifugal gel filtration on Sephadex G-25 equilibrated with 0.1M sodium phosphate, pH 6.8, and 1 mM EDTA. The resulting thionitrobenzoate derivatives of the Fab' monomers are relatively stable and can be stored for several days without significant decomposition.

One of the thionitrobenzoate derivates of Fab' monomer (derived from the anti-avidin antibody) is then converted back to the free thiol form (complexed with dithiol) by incubating for 30 minutes at 25° C. with 10 mM mercaptoethylamine in 10 mM sodium arsenite, 1 mM EDTA, and 0.1M sodium phosphate, pH 6.8. The excess mercaptoethylamine and low molecular weight reaction products are then removed by centrifugal gel filtration on Sephadex G-25 equilibrated with 0.1M sodium phosphate, pH 6.8, 1 mM sodium arsenite, and 1 mM EDTA.

The resulting anti-avidin F(ab')-thiol is then contacted immediately with an equimolar amount of the thionitrobenzoate derivative of the anti-β-galactosidase Fab', at a protein concentration of 0.5 mg/ml or higher, for 3–20 hours at 25° C., to allow formation of bispecific $F(ab')_2$. The mixture is then supplemented with solid DTNB to a final concentration of 5 mM and left for 3 hours at 25° C. to promote dissipation of any non-covalent dimeric material. Homogenous bispecific antibody determinant against avidin and β-galactosidase is then prepared by separating the $F(ab')_2$ fraction from residual Fab' monomers by high performance liquid chromatography on TSK 3000 SW in 0.1M sodium phosphate, pH 6.8, a procedure which does no damage to the $F(ab')_2$, and does not require its being chemically bonded to anything else, minimizing the risk for conformational changes which could affect activity. The formation of the desired bispecific antibody determinant can be conveniently demonstrated by its ability to cause the avidin-dependent binding of β-galactosidase to disks of biotin-substituted cellulose.

The bispecific antibody determinant can be coupled to a biotin-substituted cellulose membrane, in an arrangement such as that illustrated in FIG. 2, in an assay for a compound, e.g., lactose, which β-galactosidase can help measure (as is explained in more detail below).

Anti-β-galactosidase can be immobilized on the biotin (3 in FIG. 2) substituted membrane (4 in FIG. 2) by simply contacting the membrane (which has avidin, A, bonded to the biotin) with the bispecific determinant having an anti-avidin (A') half and an anti-β-galactosidase (C') half, and with β-galactosidase (C). In a similar manner, glucose oxidase (D) can be immobilized to membrane 4.

Using the same procedure described above, two bispecific molecules can be made, the first having specificity for a unique antigenic site on the enzyme glucose oxidase and for an antigenic site on β-galactosidase, and the second having specificity for a different antigenic site on glucose oxidase and for an antigenic site on Type I collagen. These can be used to form an electrode for measuring lactose, arranged as illustrated in FIG. 3, as follows.

First, a collagen membrane shaped to fit over a commercial $O_2$ electrode is prepared by electrolysis of a collagen fibril suspension using platinum electrodes, as described in Karube et al. (1972) Biochem. Biophys. Res. Comm. 47, 51–54, hereby incorporated by reference. Alternatively, commercially available collagen films can be used (Bardeletti et al. (1984) Anal. Chem. 56, 591).

A solution is prepared of the second bispecific antibody determinant, above, together with a 10-fold or higher molar excess of glucose oxidase, in 0.1M phosphate buffer, pH 7.0; the glucose oxidase need not be pure. The collagen membrane is immersed in this solution and incubated for 1 h at 20° C., after which time it is rinsed with buffer and then transferred to a solution containing the first bispecific antibody determinant, above, together with a 10-fold or higher molar excess of β-galactosidase in 0.1M phosphate buffer, where it is incubated at 20° C. for 1 h. The membrane is then quickly rinsed in buffer and stabilized by immersion in 0.5% glutaraldehyde in 0.1M phosphate buffer, pH 7.0, for 3 minutes.

The membrane is then placed over the oxygen-permeable teflon membrane of the commerical $O_2$ electrode, rendering the electrode ready for use for the measurement of lactose, in a manner analogous to the method of measuring sucrose described in Satoh et al. (1976) Biotechnol. and Bioengineering 18, 269–272. A sample containing an unknown amount of lactose is contacted with the membrane, and the immobilized β-galactosidase catalyzes the breakdown of the lactose into glucose, which is then acted on by the immobilized glucose oxidase to consume $O_2$, which consumption is measured as a measure of lactose in the sample.

In the preparation of the membrane described above, molar excesses of enzyme over antibody should be employed because β-galactosidase and glucose oxidase are each composed of several identical subunits. An excess of enzyme assures that, on average, only a single antigenic site on each enzyme molecule is involved in complex formation. In the preparation of other electrode using monomeric enzymes, molar excesses of enzymes are not necessary. When equimolar amounts of enzymes and bispecific antibody determinants are used, the reaction can be allowed to proceed in a single stage.

The following is a description of an example of the type of assay which employs the measurement of a substance which can be measured colorimetrically, reflectometrically, luminescently, or fluorometrically, as a measure of an unknown amount of a substance being assayed. Generally, the assay measures the amount of an unknown substance in a liquid sample, which substance is acted on by at least a first enzyme to evolve a measurable ion or compound which can be used as a measure of the unknown substance. The assay involves linking the first enzyme to a solid support (e.g. a bead or a membrane support), or to a previously sequentially acting second enzyme, by means of a bispecific antibody determinant of the invention having specificity for the first enzyme and for the support or the second enzyme. As many sequentially enzymes as are involved in the reaction sequence can be linked this way, with the last to act generally being linked to the support. The sample is contacted with the linked enzyme or enzymes immobilized on the support, and the measurable ion or compound is measured. Unknown substances which can be measured include, e.g., biomolecules such as hormones (e.g., human chorionic gonadotropin, measured in pregnancy tests), insulin, and blood sugar.

Figure 5:
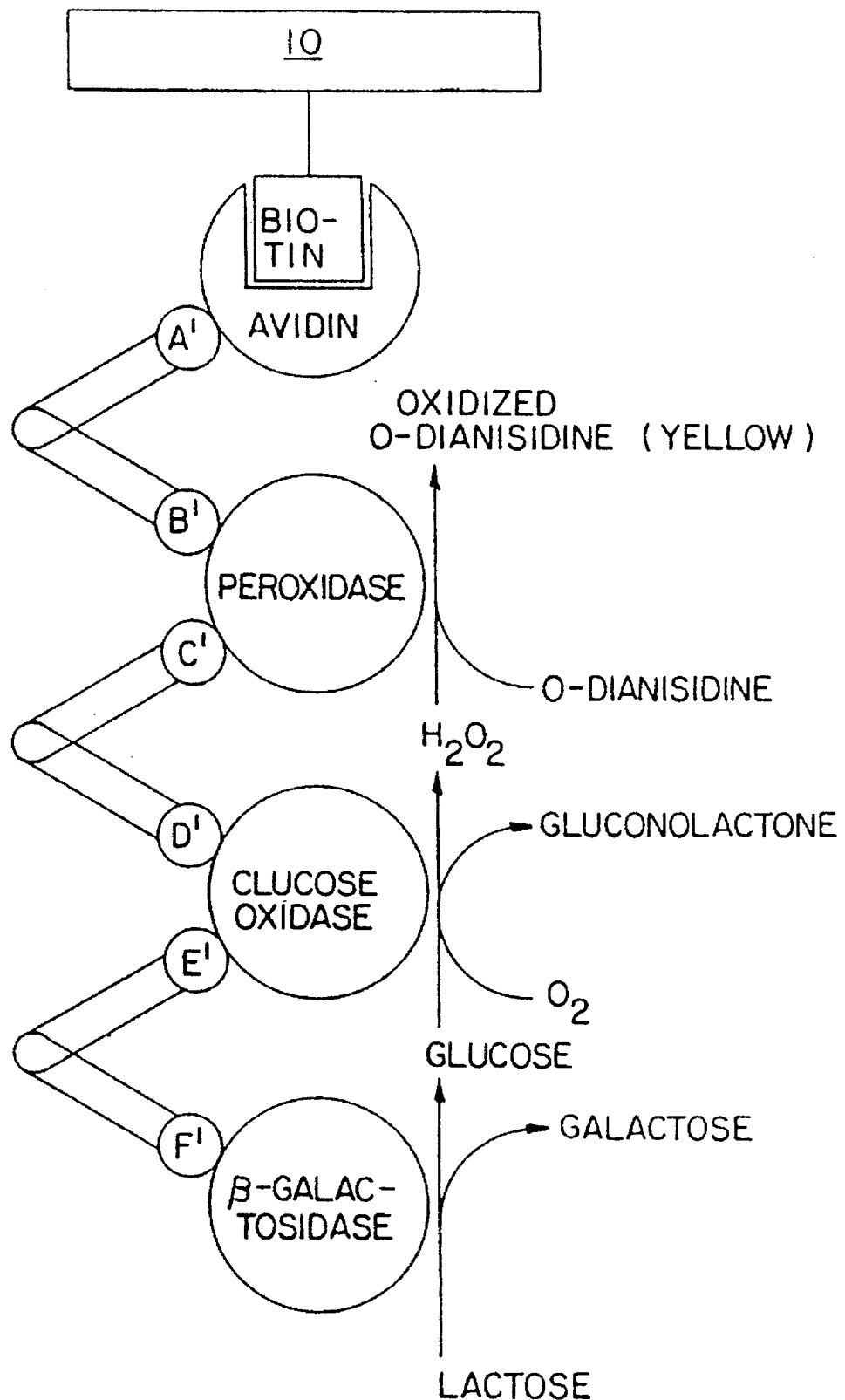
FIG. 5 is a diagrammatic representation of a multilamellar assembly useful for an assay method.

FIG. 5 is a diagrammatic representation of a colorimetric indicator for a lactose assay. Biotinsubstituted regenerated cellulose membrane 10 is used as the support for the immobilized enzymes which participate in the series of reactions by which lactose in a sample generates $H_2O_2$ to produce a colorimetrically measurable result, which is a measure of the amount of lactose in the sample.

The enzymes are immobilized, as shown in FIG. 5, by being bonded to three different bispecific antibody determinants, prepared according to the procedure described above. The first determinant has one site, A', specific for an antigenic site on the protein avidin, and the other site, B', specific for an antigenic site on the enzyme horseradish peroxidase. The second determinant has a site, C', specific for a different antigenic site on horseradish peroxidase, and the second site, D', specific for an antigenic site on glucose oxidase. The third determinant has an antibody site E', specific for a different antigenic site on glucose oxidase, and the second site, F', specific for an antigenic site on β-galactosidase.

Substituted cellulose membrane 10 can be prepared by the cyanogen bromide procedure, e.g. Cuatrecasas et al. (1968) Proc. Nat'l. Acad. Sci. USA 61, 636–643, or, more preferably, by the method of Kohn and Wilchek (1982) Biochem. Biophys. Res. Comm. 107, 878–884 as follows. Regenerated cellulose membranes (1 gram) are suspended in 25 ml of 60% acetone at −15° C. and treated with 6 ml of 1M CNBr, followed by the addition with constant stirring of 6 ml of 1.5M triethylamine in 60% acetone over a 2-minute period, during which the temperature is kept at −15° C. 100 ml of 0.1M HCl in 50% acetone is then added, and the membranes are then washed successively with 60% acetone, 30% acetone, water, and 0.2M $NaHCO_3$. The cellulose membranes are then incubated at 4° C. for 20 h in 0.2M $NaHCO_3$, pH 9, containing 1 mg per ml of ε-N-biotinyl-L-lysine (Bayer et al. (1974) Methods in Enzymology 34B, 265–267), followed by extensive washing with water.

The biotin-substituted cellulose membrane is then immersed in 0.1M phosphate buffer, pH 7.0, and incubated for 1 h at 20° C. with approximately equivalent molar amounts of avidin, horseradish peroxidase, and the bispecific antibody determinant having sites A' and B'. The membrane is then rinsed with buffer and transferred to a solution containing an approximately equivalent molar amount of the bispecific antibody determinant having sites C' and D', and a 10-fold molar excess of glucose oxidase. After 1 hour at 20° C. the membrane is rinsed with buffer and transferred to a solution containing an approximately equivalent molar amount of the bispecific antibody determinant having sites E' and F', and a 10-fold molar excess of β-galactosidase, and incubated at 20° C. for 1 h. followed by rinsing with buffer. If repeated use is anticipated, the membrane is stabilized by immersion in 10 mM dimethyl suberimidate in 0.1M triethanolamine buffer. pH 8.1, for 1 hour.

The enzymes used in the above-described procedure need not be pure. In the example described, a molar excess of β-galactosidase and glucose oxidase is necessary because these enzymes are composed of several identical subunits. In cases where only monomeric enzymes are used, molar excesses of enzymes are not necessary. When equimolar amounts of enzymes and bispecific antibody determinants are used, the reaction can be allowed to proceed in a single stage.

For the determination of lactose, membrane 10 is immersed in or wetted with a sample containing an unknown amount of lactose in 0.1M phosphate buffer, pH 7, and 0.01% o-dianisidine.

As shown in FIG. 5, lactose in the sample first acts on β-galactosidase to form glucose, which in turn is acted on by glucose oxidase, in the presence of oxygen, to release $H_2O_2$, which, with peroxidase, oxidizes o-dianisidine to produce a yellow dye with absorbance at 460 nm. Various other chromogenic or fluorogenic substances, e.g., leukodyes, can be substituted for o-dianisidine.

Figure 6:
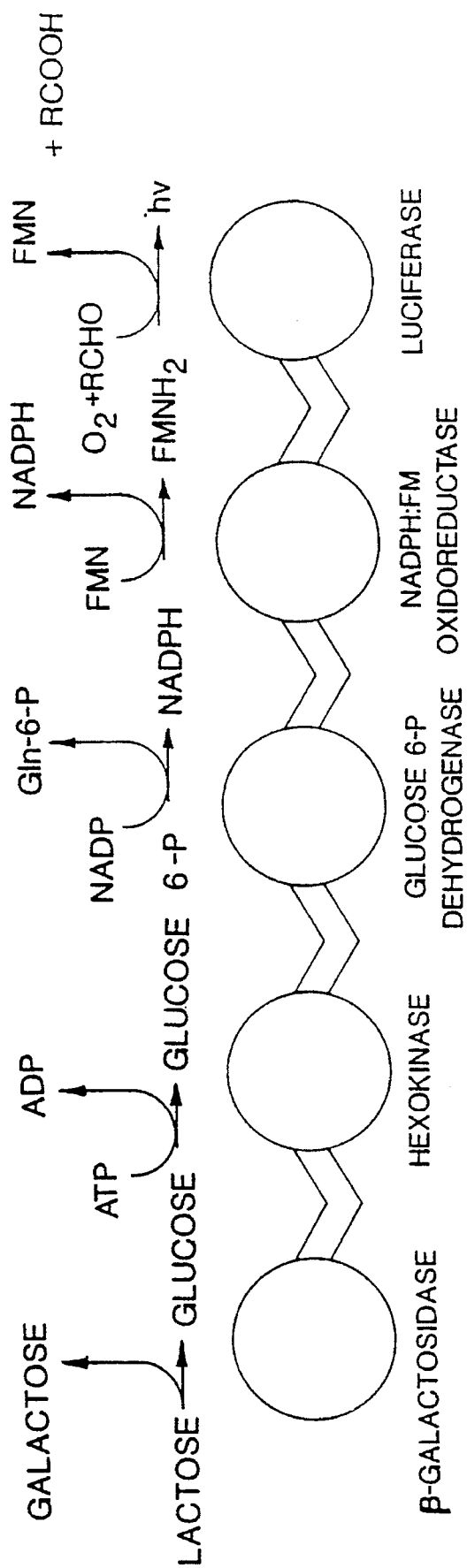
FIG. 6 is a diagrammatic representation of an assembly useful in a bioluminescence assay.

FIG. 6 illustrates an alternative arrangement of self-assembling enzymes linked by bispecific antibody determinants (shown as chevrons linking circular enzymes). As in the arrangement of FIG. 5, the last enzyme in the sequence (luciferase) can be immobilized using, e.g. avidin and a biotin-substituted membrane (not shown). Luciferase, when reduced as shown, is bioluminescent (the reaction chain shown is described in greater detail in Wienhausen and DeLuca (1982) Anal. Biochem. 127, 380, and Hastings et al. U.S. Pat. No. 4,278,761, hereby incorporated by reference).

FIG. 7 illustrates a "channeling" immunoassay which employs two bispecific monoclonal antibody determinants. (The illustrated assay employs some of the principles of the channeling immunoassay described in Litman et al. (1980) Anal. Biochem. 106, 223). The first bispecific determinant has specificity for a first enzyme and for a first antigenic site on an antigen being measured, e.g. human chorionic gonadotropin. The second bispecific determinant has specificity for a second enzyme and for a second antigenic site on the antigen being measured. The first enzyme is capable of acting on a first substrate to produce a second substrate which can be acted on by the second enzyme to evolve a measurable compound or ion. The assay is carried out by contacting the liquid mixture suspected of containing the molecule to be measured with the two bispecific determinants and the two enzymes, in the presence of the first substrate. If the unknown is present, the two determinants will bind to it and the two enzymes bound to them will be brought very close together, so that the efficiency of the two reactions is increased by orders of magnitude. In the illustrated scheme, the first enzyme is glucose oxidase, the second enzyme is peroxidase, the first substrate is glucose, and the second substrate is peroxide, which oxidizes a leukodye to produce a measurable dye. As in the arrangement of FIG. 5, the last enzyme in the sequence can be immobilized. The assay illustrated in FIG. 7 includes an optional feature for improving the signal to noise ratio, the use of a competing enzyme (in this case, catalase) in an amount large enough to swamp the action of peroxidase in the absence of the enzyme-coupling unknown substance.

FIG. 8 illustrates a fluorescent energy transfer immunoassay analogous to the assay of FIG. 7; the difference is that in the energy transfer assay, light, rather than organic substrates, is sequentially acted on to produce a measurable result. The assay employs two fluorescent proteins, in the illustrated assay, these are phycoerythrin ("Phy") and allophycocyanine ("All"), both produced by blue-green algae and described, as being useful in immunoassays, in Glazer and Stryer (1983) Biophys. J. 43, 323, hereby incorporated by reference. As illustrated in FIG. 8, one bispecific monoclonal antibody determinant has specificity for a first site on the antigen being assayed (e.g. human chorionic gonadotropin) and for Phy, and the second bispecific monoclonal antibody determinant has specificity for a second site on the antigen and for All. Presence of the antigen closely couples Phy and All, greatly increasing energy transfer efficiency. The signal is produced because Phy excites at 500 nm and transmits at 580 nm, while All is transparent to 500 nm but excites at 580 nm and transmits at 660 nm. Thus the 660 nm signal is only achieved by the sequential passage of light through both proteins, a process whose efficiency depends on proximity of the proteins. As in the assays described above, one or both fluorescent proteins can be immobilized on a support, either by conventional means or via bispecific determinants of the invention.

Figures 12A, 12B:
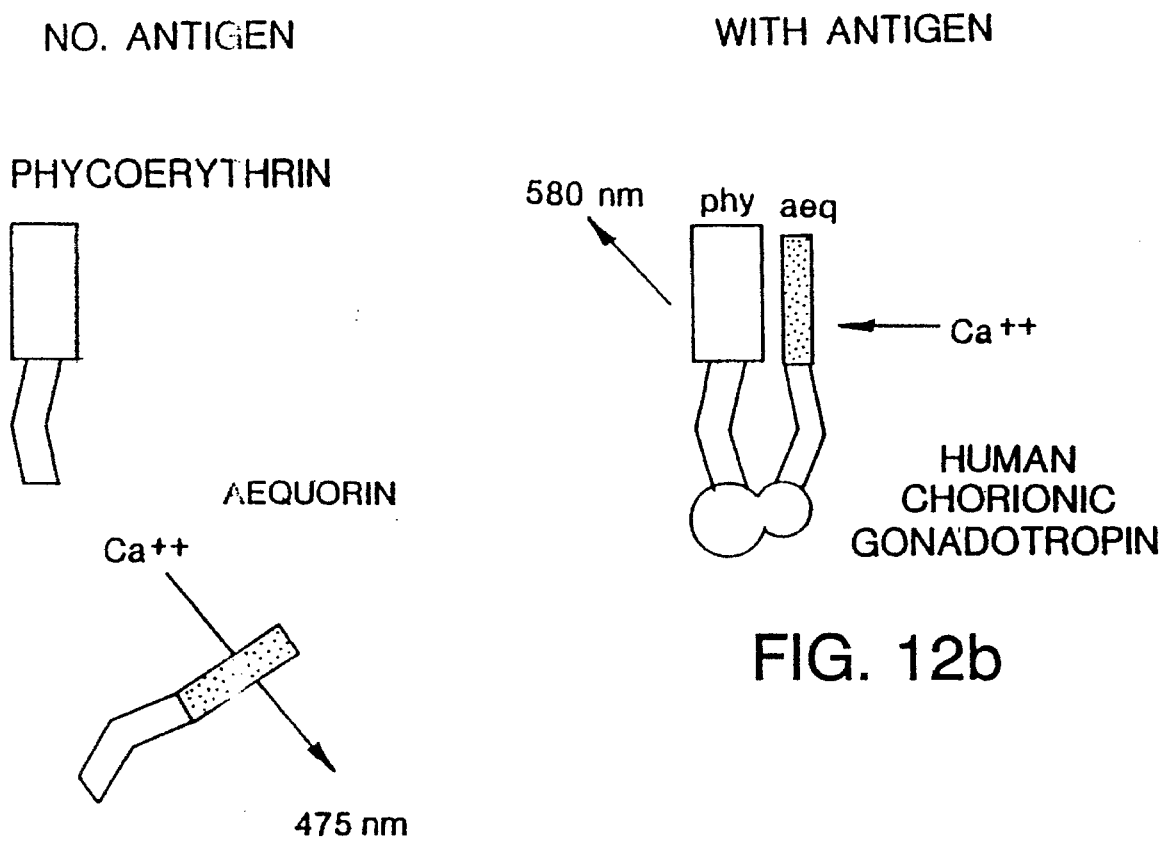
FIG. 12 is a diagrammatic representation of a luminescent energy transfer immunoassay employing bispecific monoclonal antibody determinants.

A closely related type of immunoassay, illustrated in FIG. 12, involves luminescence energy transfer between a luminescent molecule and a fluorescent substance, as in Patel et al. (1983) Analytical Chemistry 129, 162–169. Referring to FIG. 12, the luminescent protein aequorin is used in conjunction with phycoerythrin. The presence of the antigen closely couples aequorin and phycoerythrin, greatly increasing energy transfer efficiency. The addition of $CA^{++}$ elicits the luminescence of aequorin at 475 nm, which excites phycoerythrin and causes it to emit fluorescence at 580 nm. Thus the 580 nm signal is only achieved by the wavelength modulation of aequorin luminescence by phycoerythrin, a process whose efficiency depends on the proximity of the proteins.

Other embodiments are within the following claims. For example, although $IgG_1$ antibodies are preferred, $IgG_2$ and IgA antibodies can also be used in the invention. Also, the entire half-molecule, rather than just the F(c') portion, can be used. Yield can be improved slightly by using, as the dithiol complexing agent, instead of sodium arsenite, 0.25 mM phenylarsine oxide.

What is claimed is:

1. A method of preparing a bispecific monoclonal antibody comprising the steps of providing samples of two different monoclonal antibodies or fragments thereof, each said antibody or antibody fragment recognizing a different antigenic determinant and comprising two identical L-H half-molecules linked by one or more disulfide bonds, subjecting each said sample of antibodies or antibody fragments to reducing conditions sufficient to break said disulfide bonds linking said L-H half-molecules, whereby each said antibody or antibody fragment is split into two identical reduced half-molecules, derivatizing the reduced half-molecules in one of said samples with a thiol activating agent to form a sample of activated half-molecules which are capable of facilitating the formation of disulfide bonds, the reduced half-molecules in the other of said samples not being activated, and combining said sample of reduced half-molecules with said sample of activated half-molecules under conditions which permit said reduced half-molecules to form said bispecific antibodies by the formation of one or more disulfide bonds with said activated half-molecules.

2. The method of claim 1 wherein said thiol activating agent prevents the recombination of said thiol activated identical half-molecules.

3. The method of claim 1 wherein said two different antibodies or antibody fragments are IgG or IgA.

4. The method of claim 3 wherein said two different antibodies or antibody fragments are IgG.

5. The method of claim 3 wherein said two different antibodies or antibody fragments are IgG2A, IgG2B, or IgG3.

6. The method of claim 1 wherein each different half-molecule consists of the F(ab') portion of an IgG antibody.

7. The method of claim 6 wherein one of the said monoclonal IgG F(ab')2 portions comprises two identical L-H half-molecules linked by more than one disulfide bond, and said step of splitting said IgG F(ab')2 portions into half-molecules is carried out under conditions which prevent the formation of disulfide bonds within the H chains of said half-molecules.

8. The method of claim 7 wherein both said monoclonal antibody portions comprise two identical L-H half-molecules linked by more than one disulfide bond, and splitting of both portions into half-molecules is carried out under conditions which prevent the formation of disulfide bonds within the H chains of said half-molecules.

9. The method of claim 7 or claim 8 wherein the formation of said disulfide bonds within said H chains is prevented by carrying out said splitting in the presence of a dithiol complexing agent.

10. The method of claim 9 wherein said dithiol complexing agent comprises an arsenite.

11. The method of claim 10 wherein said arsenite comprises an inorganic arsenite.

12. The method of claim 11 wherein said inorganic arsenite comprises sodium arsenite.

13. The method of claim 10 wherein said arsenite comprises an aryl arsenite.

14. The method of claim 13 wherein said aryl arsenite comprises phenylarsine oxide.

15. The method of claim 9 wherein said dithiol complexing agent comprises a cadmium salt.

16. The method of claim 7 or claim 8 wherein the formation of said disulfide bonds within said H chains is prevented by carrying out said splitting under conditions under which the conformation of said H chains is modified to prevent said disulfide bond formation.

17. The method of claim 16 wherein the formation of said disulfide bonds within said H chains is prevented by carrying out said splitting at a pH between 3.8 and 4.5.

18. The method of claim 17 wherein said pH is about 4.2.

19. The method of claim 7 or claim 8 wherein the formation of said disulfide bonds within said H chains is prevented by, following said splitting, removing all but one reduced cysteine residues using a proteolytic enzyme.

20. The method of claim 19 wherein said proteolytic enzyme comprises carboxypeptidase Y.

21. The method of claim 1 wherein said thiol activating agent comprises an aromatic disulfide.

22. The method of claim 21 wherein said aromatic disulfide comprises 5,5'-dithiobis (2-nitrobenzoic acid).

23. The method of claim 21 wherein said aromatic disulfide comprises 2,2'-dipyridine disulfide.

24. The method of claim 21 wherein said aromatic disulfide comprises 4,4-dipyridine disulfide.

25. The method of claim 1 wherein said thiol activating agent comprises a mixture of sulfite and thiosulfite.

26. The method of claim 1 wherein both F(ab') half-molecules are derivatized with a thiol activating agent, and one of said half-molecules is then converted to the available thiol-containing form by subsequent reduction of the thiol-activated F(ab') to the free thiol.

27. The method of claim 26 wherein said subsequent reduction is carried out under conditions which prevent the formation of disulfide bonds within the H chains of said half-molecules.

28. The method of claim 27 wherein the formation of said disulfide bonds within said H chains is prevented by carrying out said splitting in the presence of a dithiol complexing agent.

29. A method of preparing a homogeneous sample of identical bispecific antibodies, said method comprising the steps of providing samples of two different monoclonal IgG antibodies or fragments thereof, each said antibody or antibody fragment comprising two identical L-H half-molecules linked by one or more disulfide bonds, each said L-H half molecule comprising at least the F(ab')2 portion of said monoclonal IgG antibody, subjecting said antibodies or antibody fragments in each sample to conditions sufficient to break said disulfide bonds linking said L-H half-molecules, whereby said antibodies or antibody fragments in each said sample are split into two half-molecules, derivatizing the half-molecules in one of the two samples with a thiol activating agent which facilitates the formation of disulfide bonds between said thiol activated half-molecules and said different half-molecules and which prevents said thiol activated half-molecules from recombining with each other, forming a mixture by combining said samples under conditions which permit at least some thiol activated half-molecules to chemically combine with at least some of said different half-molecules to form said identical bispecific antibodies, and separating said identical bispecific antibodies from said mixture.

30. The method of claim 29 wherein said separation step comprises separation of said bispecific antibodies from unreacted half-molecules.

31. The method of claim 30 wherein said separation step comprises separation on the basis of molecular size.

32. The method of claim 31 wherein said separation step comprises gel filtration.

33. The method of claim 29 wherein said separation step comprises ion-exchange, electrophoresis, isoelectric focusing, or affinity chromatography.

34. An assay for measuring the amount of an unknown substance in a liquid sample, which substance is acted upon by at least a first enzyme to evolve a measurable ion or compound, said ion or compound evolved being a measure of said substance, said assay comprising a) linking said first enzyme to a solid support or to a second enzyme which produces a substrate for said first enzyme by means of a homogeneous preparation of the antibody prepared by the method of claim 1 comprising two L-H half-molecules linked by disulfide bonds, each said half-molecule being different from the other and comprising at least the F(ab') portion of a monoclonal IgG antibody, one said L-H half-molecule being specific for an antigenic site on said first enzyme molecule, the other half-molecule being specific for an antigenic site on said support or on said second enzyme, b) contacting said sample with said bispecific monoclonal antibody linking said first enzyme and said second enzyme or said support, and c) measuring said measurable ion or compound as a measure of said unknown substance in said sample.

35. The assay of claim 34 wherein said measurable ion or compound is measured by measuring fluorescence, color, or luminescence.

36. A channeling immunoassay for measuring an antigen in a liquid sample comprising
1) providing two homogeneous preparations of the antibody prepared by the method of claim 1,
the first having specificity for a first antigenic site on said antigen being measured and for a first enzyme,
the second having specificity for a second antigenic site on said antigen being measured and for a second enzyme,
said first enzyme being capable of acting on a first substrate to evolve a second substrate capable of being acted on by a said second enzyme to produce a measurable ion or compound,
2) contacting said first and second bispecific monoclonal antibodies and said first and second enzymes with said sample in the presence of said first substrate, and
3) measuring said measurable ion or compound as a measure of said antigen being measured.

37. The channeling immunoassay of claim 36 in which one of the enzymes is linked to a solid support by a bispecific antibody of which one L-H half-molecule is specific for an antigenic site on said enzyme, the other half-molecule being specific for an antigenic site on said support.

38. The immunoassay of claims 36 or 37 wherein said first enzyme is glucose oxidase, said second enzyme is peroxidase, said first substrate is glucose, and said second substrate is peroxide.

39. The immunoassay of claims 36 or 37 wherein said measurable ion or compound is measured by measuring fluorescence, color, or luminescence.

40. A fluorescence energy transfer immunoassay for measuring an antigen in a liquid sample comprising
1) providing two homogenous preparations of the antibody prepared by the method of claim 1,
the first having specificity for a first antigenic site on said antigen being measured and for a first fluorescent antigen,
the second having specificity for a second antigenic site on said antigen being measured and for a second fluorescent antigen,
the first fluorescent antigen being capable of absorbing light at a first wavelength at which the second fluorescent antigen has little absorption and emitting fluorescence at a second wavelength capable of being absorbed by said second fluorescent antigen, said second fluorescent antigen being capable, upon absorption of light of said second wavelength, of fluorescence at a third wavelength at which said first fluorescent antigen has little absorption,
2) contacting said first and second bispecific monoclonal antibodies and said first and second fluorescent antigens with said sample,
3) passing light of said first wavelength through said mixture, and
4) measuring the amount of light emitted at said third wavelength as a measure of said antigen being measured.

41. The immunoassay of claim 40 wherein said first fluorescent antigen comprises phycoerythrin, said second fluorescent antigen comprises allophycocyanine, said first wavelength is approximately 500 nm, said second wavelength is approximately 580 nm, and said third wavelength is approximately 660 nm.

42. A luminescence energy transfer immunoassay for measuring an antigen in a liquid sample comprising
1) providing two homogeneous preparations of the antibody prepared by the method of claim 1,
the first having specificity for a first antigenic site on said antigen being measured and for a luminescent antigen,
the second having specificity for a second antigenic site on said antigen being measured and for a fluorescent antigen,
the luminescent antigen being capable of emitting light at a first wavelength which is capable of being absorbed by the fluorescent antigen, the fluorescent antigen being capable, upon absorption of light of said first wavelength, of emitting fluorescence at a second wavelength at which said luminescent antigen has little absorption,
2) contacting said antibody determinants and said luminescent and fluorescent antigens with said sample,
3) eliciting the luminescence of the luminescent antigen, and
4) measuring the amount of light emitted at said second wavelength as a measure of said antigen being measured.

* * * * *

UNITED STATES PATENT AND TRADEMARK OFFICE
CERTIFICATE OF CORRECTION

PATENT NO. : 5,523,210
DATED : June 4, 1996
INVENTOR(S) : Henry P. Paulus

It is certified that error appears in the above-indentified patent and that said Letters Patent is hereby corrected as shown below:

On title page, item [56]

Under "OTHER PUBLICATIONS", replace "Glennie et al." (second occurrence) to read --Preparation and Performance of Bispecific F(ab'$\gamma$)$^2$ Antibody Containing Thioether-Linked Fab'$\gamma$ Fragments...--;

On title page, item [56], second column, "Nisonoff and Rivers", correct the spelling of "Biochem.";

Column 2, line 60, correct the spelling of "cystine";

Column 16, claim 41, line 19, correct the spelling of "allophycocyanin".

Signed and Sealed this

Second Day of December, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,523,210

DATED : June 4, 1996

INVENTOR(S) : Henry P. Paulus

It is certified that error appears in the above-identified patent and that said Letters Patent is hereby corrected as shown below:

```
Column 13, claim 7, line 10, replace "F(ab') 2 portions"
with --F(ab') portions--;

Column 13, claim 7, line 13, replace "F(ab') 2 portions"
with --F(ab') portions--;
```

Signed and Sealed this

Ninth Day of June, 1998

Attest:

BRUCE LEHMAN

Attesting Officer

Commissioner of Patents and Trademarks